United States Patent [19]

Liav et al.

[11] 4,307,229

[45] Dec. 22, 1981

[54] 6,6'-DIESTERS OF TREHALOSE AND PROCESS FOR THE SYNTHESIS THEREOF

[76] Inventors: Avraham Liav, Apt. 101, 1650 S. Albion St., Denver, Colo. 80222; Mayer B. Goren, 125 Locust St., Denver, Colo. 80220

[21] Appl. No.: 91,194

[22] Filed: Nov. 7, 1979

[51] Int. Cl.$^3$ .................. C07H 13/02; C07H 13/12; A61K 31/70
[52] U.S. Cl. .................. 536/119; 424/180; 536/115; 536/122; 536/120
[58] Field of Search ............... 536/119, 120, 115, 122

[56] References Cited

U.S. PATENT DOCUMENTS

| | | | |
|---|---|---|---|
| 3,956,278 | 5/1976 | Prey | 536/119 |
| 4,002,609 | 1/1977 | Khan | 536/119 |
| 4,107,425 | 8/1978 | Pfeffer et al. | 536/119 |
| 4,117,224 | 9/1978 | Khan et al. | 536/119 |

*Primary Examiner*—Johnnie R. Brown
*Attorney, Agent, or Firm*—L. S. Van Landingham, Jr.

[57] ABSTRACT

An improved process is described for synthesizing simple and complex 6,6'-diacyl esters of trehalose and intermediates useful therein. Novel 6,6'-diacyl esters of trehalose and novel intermediates useful in the process of the invention are also disclosed. The inventive process is capable of producing the desired compounds economically and in pure form from readily available starting materials.

35 Claims, No Drawings

6,6'-DIESTERS OF TREHALOSE AND PROCESS FOR THE SYNTHESIS THEREOF

The United States Government has rights in this invention pursuant to Grant No. AI-08401-12 awarded by the Dept. of Health, Education and Welfare, covering the period from Sept. 1, 1979 through Aug. 31, 1980.

THE BACKGROUND OF THE INVENTION

1. The Field Of The Invention

This invention broadly relates to an improved process for synthesizing 6,6'-diacyl esters of trehalose. The invention is also concerned with novel 6,6'-diacyl esters of trehalose. In further variants, the invention relates to novel intermediates which are useful in the synthesis of 6,6'-diacyl esters of trehalose and to an improved process for the preparation thereof.

2. The Prior Art

As is well known by those skilled in this art, alpha-D-glucopyranosyl-(1,1)-alpah-D-glucopyranoside is often referred to as trehalose. Naturally occurring 6,6'-diesters of trehalose with a variety of "mycolic acids" have been isolated from numerous species of Mycobacteria, Corynebacteria and Nocardia. The mycolic acids obtained from these natural sources are alpha-branched beta-hydroxy acids ranging in the number of carbon atoms that they contain from about 32 as found in Corynebacteria, to the more than 90 carbon atoms that are characteristic of such Mycobacteria as *M. tuberculosis, M. bovis, M. avium* and others.

The natural trehalose-6,6'-dimycolates were once believed to be associated with the unusual morphology characteristic of virulent species of *M. tuberculosis* to grow in culture in the form of serpentine cords. As a result, they are known by the trivial name "cord factor" [see Reviews: *Tubercle* 56:65-71 (1975); and *Chemistry and Physics of Lipids*, 16:91-106 (1976)]. Naturally occurring trehalose mycolates that were prepared and purified by high pressure liquid chromatography have been given the designation "P3", and these are also cord factors as has been proven by permethylation analysis and examination by nuclear magnetic resonance [see *Biochimica Biophysica Acta* 574:64-69 (1979)]. Thus, the terms natural trehalose-6,6'-dimycolate, "cord factor", and "P3" may be referred to herein interchangeably as they have substantially identical meanings. However, it is understood that numerous types of mycolic acids are present in natural cord factor samples, and it is not yet possible to assign a single unique structure to the natural cord factors. For the purpose of this invention, the synthetic cord factors and their simpler analogs disclosed herein are intended to be restricted to the 6,6'-diacyl esters of trehalose. They may be symmetrically or unsymmetrically substituted with acyl substitutents containing from as few as about 10 carbon atoms to as many as about 100 carbon atoms.

It is well known that natural cord factor has a number of biological activities, which are described in greater detail hereinafter. However, natural cord factor is very difficult to obtain and purify sufficiently for therapeutic and other purposes. Even the best prior art purification techniques produce products which often contain residues of bacterial components, such as cell wall debris, proteins, membranes, and the like. These bacterial contaminants may provoke very undesirable side effects, including sensitization, toxicity, fever, malaise and even death. As a result, the prior art has long sought a facile and versatile synthesis of trehalose-6,6'-diacyl esters, including the dimycolates.

A number of attempts have been made heretofore to synthesize cord factors. In one early prior art synthesis, which is described in *Bulletin Societe Chimie de France* (1956) 1471-1478, trehalose was converted with para-toluene sulfonyl chloride into a reaction product which was reported as being 6,6'-ditosyl trehalose. However, as is shown in *Carbohydrate Research* 44:308-312 (1975), it is now known that most of this product is actually the 6,2-ditosylate. The 6,6'-derivative may be purified from the 6,2 derivative only with great difficulty and in low yield, and it is condensed with potassium mycolate by prolonged heating (80 hours) in dimethylformamide as a solvent to give very low yields of trehalose-6,6'-di mycolate. The high reaction temperatures that are necessary result in the formation of 3,6 -anhydro derivatives of the trehalose core, as is disclosed in *Chemistry and Physics of Lipids* 16:91-106(1976), and *Carbohydrate Research* 44:308-312 (1975). The aforementioned condensation step has recently been improved by carrying out the reaction at a lower temperature in toluene in the presence of "Crown ethers" as disclosed in *Carbohydrate Research* 65:295-300(1978). Nevertheless, the difficulty in preparing pure trehalose-6,6'-ditosylate has been and remains a serious drawback to the successful exploitation of this process as disclosed in *Biochimie* 55:569-573 (1973). Some anhydrotrehalose derivative is still formed and the separation of the cord factor product from the residual mycolic acid is very difficult and impure reaction products are the general rule. The present inventors examined a semicommercial synthetic cord factor product that was carefully prepared according to the methods described above and found that it contained no more than 50-60% of the desired reaction product, and thus the remaining 40-50% was impurities.

In another prior art synthesis, 6,6'-dibromo-6,6'-didesoxy trehalose was prepared in 62% yield according to the method of Hanessian, as disclosed in *Carbohydrate Research* 24: 45-56 (1972), and then converted to the 2,3,4,2',3',4'-hexa-O-trimethylsilyl derivative in a yield of 72%, which was then condensed at 70° C. with sodium mycolate in hexamethylphosphoric triamide to prepare hexatrimethylsilylated cord factor. After de-trimethylsilylation and chromatography on silica gel, the desired cord factor product was obtained in a yield of 33% for the final step and the overall yield was only 15%, as disclosed in *Carbohydrate Research* 44:308-312 (1975). In this last step, the chromatographic separation of the cord factor product from contaminating mycolic acid was especially difficult, as is disclosed in *Advances in Tuberculosis Research* 7:149-183 (1956), and in *Recent Results in Cancer Research* 47:251-258 (1974). From the standpoint of yields obtained, and especially when the operational difficulties encountered in the purification of the intermediate and final products are taken into consideration, the prior art syntheses are unsatisfactory.

In view of the above discussion of the prior art, it is apparent that there has been a great and long existing need for an improved process for preparing the natural cord factors and other 6,6'-diacyl trehaloses, which avoids the many complications and deficiencies of the prior art processes, and produces the desired reaction products at low cost and in a substantially pure form permitting their use for therapeutic and other biological purposes without provoking undesirable side effects.

However, an entirely satisfactory synthesis was not available prior to the present invention.

THE SUMMARY OF THE INVENTION

The present invention overcomes the aforementioned deficiencies and disadvantages of the prior art, and provides for the first time an entirely satisfactory process for synthesizing both the simple and complex 6,6'-diacyl esters of trehalose. This is accomplished by providing versatile reactions which produce higher overall yields and which facilitate chromatographic purification of the novel intermediate and final reaction products. The unique properties of the novel intermediate and final reaction products greatly aid in avoiding difficult purifications, formation of unwanted isomers, and production of anhydrotrehalose derivatives as by-products. As a result, the process of the invention is capable of producing 6,6'-diacyl esters of trehalose economically and in forms sufficiently pure for therapeutic and other biological purposes.

The synthesis of the present invention may use mycolic acids derived from natural sources that have been purified so as to be free of bacterial contaminants. This is of great importance as synthetic cord factors, or the trehalose-6,6'-dimycolates described herein, may be prepared which are substantially identical in their biological activities to the natural cord factors. Inasmuch as it is relatively easy to purify natural mycolic acids, as compared with the purification of natural cord factor, so as to be in forms equally free of deleterious proteins, cell wall constituents and other lipids, it is apparent that the synthesis of the present invention is very desirable.

In one presently preferred variant of the inventive process, 6,6'-ditrityl-trehalose is converted to the hexa-O-benzyl derivative to block the free hydroxyl groups, and then a very specific detritylation is performed to open the 6,6'-hydroxyl positions. Thereafter, 2,3,4,2',3',4'-hexa-O-benzyl-6,6'-diesters of trehalose are prepared by either of two alternative processes discussed more fully hereinafter, followed by dehexabenzylation by hydrogenolysis to produce the desired 6,6'-diacyl esters of trehalose. This presently preferred variant provides novel intermediate compounds, i.e., the above 2,3,4,2',3',4'-hexa-O-benzyl derivatives of trehalose, which have unusual and unexpected properties in the disclosed synthesis of 6,6'-diacyl esters of trehalose, and it further provides novel 6,6'-diacyl esters of trehalose which have unusual and unexpected properties, including a number of biological properties which are discussed in greater detail hereinafter.

It will be appreciated that the present invention has certain other preferred variants and embodiments. These preferred variants and embodiments will be discussed in greater detail hereinafter, and thus they will be apparent upon considering the following detailed description of the invention. The present invention is intended to embrace these further preferred variants and embodiments, as well as those additional variants and embodiments which will be apparent to those skilled in this art upon considering the applicants' teachings in the light of the prior art.

THE DETAILED DESCRIPTION OF THE INVENTION INCLUDING THE PRESENTLY PREFERRED VARIANTS AND EMBODIMENTS THEREOF

For the purposes of the present invention and the following discussion, the cord factors and their simpler analogs will be limited to the 6,6'-diacyl esters of trehalose having the following abbreviated structural formula

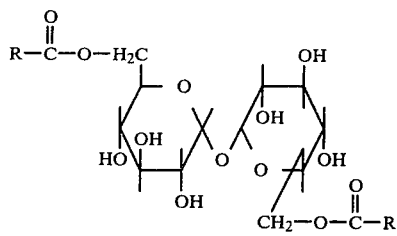

, wherein R is a monovalent organic radical which, when taken with the carbon atom attached thereto, contains about 10-100 carbon atoms and preferably about 20-90 carbon atoms, and is the residue of a saturated or unsaturated and substituted or unsubstituted carboxylic acid. The trehalose-6,6'-diacyl esters may be symmetrically or unsymmetrically substituted with the acyl substituents, and thus each R may be individually selected so as to be the same or a different monovalent organic radical within the above definition. The resulting trehalose-6,6'-diacyl esters have demonstrable biological activity when the acyl substituents contain between about 10 and 100 carbon atoms.

While the present invention is not limited thereto, it is often preferred that each monovalent organic radical R be the residue of a carboxylic acid such as: decanoic acid, lauric acid, myristic acid, palmitic acid, stearic acid, palmitoleic acid, oleic acid, eicosanoic acid, eicosenoic acid, erucic acid, tetracosanoic acid and hexacosanoic acid; the multimethyl branched carboxylic acids, derived from mycobacterial lipids, including the homologs of phthienoic acids (alpha, beta-unsaturated), homologous mycocerosic acids, homologous phthioceranic acids and homologous hydroxyphthioceranic acids (see M. Goren and P. J. Brennan in, G. P. Youmans, ed. *Tuberculosis*, W. B. Saunders Company, 1979, pages 63–193); and simple synthetic carboxylic acids such as p-hexadecyloxy-phenyl-4-butyric acid, p-octadecyloxyphenyl-4-butyric acid, 3,4-di-(hexadecyloxy)-phenyl-γ-butyric acid, and 3,4-di-(octadecyloxy)-phenyl-butyric acid. For the purposes of this invention, derivatives of phenyl-γ-butyric acid may be referred to herein as derivatives of phenyl-4-butyric acid, or as phenyl butyric acid without further limitation. It is understood that these terms are used interchangeably in the specification and claims. By Claisen condensation of methyl or ethyl esters of simple carboxylic acids, beta-keto esters are obtained, which upon reduction with $NaBH_4$, are converted into the various diastereomers of simple mycolic acids that have been recognized as constituents of Corynebacteria and Nocardia [see *Carbohydrate Research* 66:295–300 (1978)]. As an example, condensation of methyl palmitate catalyzed by NaH and a small amount of $NaOCH_3$ or $NaOC_2H_5$ in refluxing xylene yields alpha-palmitoylpalmitic acid methyl ester. $NaBH_4$ reduction converts this reaction product into a mixture of DL-erythro and DL-threo-alpha-n-tetradecyl-beta-hydroxy n-octadecanoic acid methyl ester, and these are converted by base-catalyzed hydrolysis to the corresponding carboxylic acids, which correspond to the natural corynomycolic acid and its diastereoisomers and are useful for the purpose of the present invention. Similar beta-keto esters and their reduction products can be derived from Claisen condensations of methyl or ethyl decanoate, myristate, stearate, behenate, tetracosanoate and hexacosanoate and their unsaturated analogs. The carboxylic acids derived from the foregoing Claisen condensations preferably contain about 20–60 carbon atoms.

The purified natural mycolic acids are especially useful, and synthetic trehalose-6,6'-diesters of these acids prepared according to the process of the present invention correspond to the natural cord factors isolatable from Corynebacteria, Nocardia and various mycobacteria. These synthetic cord factors are endowed with the unusual biological properties described herein for natural cord factor. The natural purified mycolic acids are obtainable from harvests of the corresponding bacteria grown in culture according to methods that have been described in the prior art and are not a part of this invention. Inasmuch as it is relatively easy to purify natural mycolic acids, as compared with the purification of natural cord factor, so as to be in forms equally free of deleterious proteins, cell wall constituents and other lipids, it is apparent that the synthesis of the present invention is very desirable. Semipurified mixed mycolic acids may be used without further purification, or they may be separated by prior art chromatographic procedures into the individual mycolate classes, such as are depicted herein in Table 1. For the purpose of the present invention, these mycolic acids may be used as mixtures or individually in the form of their solvent soluble salts and preferably as the potassium salts or sodium salts.

Two of the several types of natural mycolic acids derived from the natural cord factor of *M. tuberculosis* may be represented by the following formulae 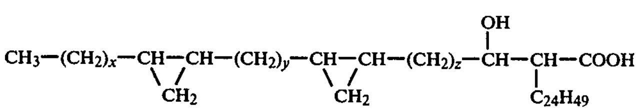 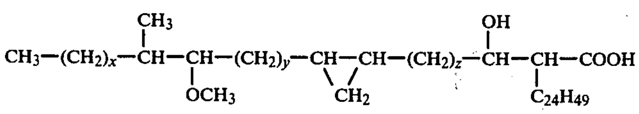 , wherein in general x, y and z have numerical values which are odd, even and odd such as, for example, 17, 14 and 17. The numerical values for x, y, and z may vary over substantial ranges for the above and the other types of mycolic acids disclosed herein. For instance, mycolic acids are known having as few as about 32 carbon atoms and as many as about 90 carbon atoms, and the carbon atom content for a given type of mycolic acid may be varied by increasing and/or decreasing the numerical values for x, y and z. Since numerous types of mycolic acids have been found in individual natural cord factor samples and are recognized, it is not yet possible to assign single unique structures to cord factor, or even to decide whether or not any individual molecule of cord factor is entirely symmetrical in its mycolate components. Because of the structural heterogeneity of the mycolates, which is amplified by the multitude of homologs differing in the individual values of x, y, and z, it is unlikely that an entirely homogeneous example of natural cord factor will be isolated in the near future.

Several additional types of mycolic acids are set forth hereafter in Table I, and invariably all of these mycolic acids are present with homology in the x, y, and z positions. The above mentioned two types of natural mycolic acids derived from the cord factor of *M. tuberculosis* and the additional types of natural mycolic acids appearing in Table I, as well as the numerous homologs thereof, are very useful in practicing the synthesis of the invention discussed hereinafter. Also, the aforementioned structural formula for cord factor may be symmetrically or unsymmetrically substituted in the 6 and 6' positions with acyl groups derived therfrom.

TABLE I

Structures of Some Mycolic Acids

| Mycolic acid | Strain |
|---|---|
| | *Corynebacterium diphtheriae* |
|  |  |
| Smegmamycolic acid | *M. smegmatis* |
|  | |
| Kansamycolic acid | *M. kansasii* |
|  | |
| Methoxylated mycolic acid | *M. tuberculosis* var. hominis, strain Test |
| 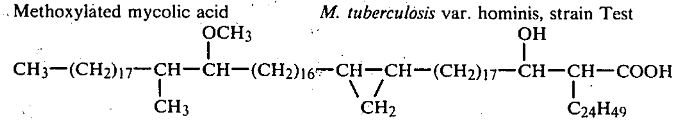  | |

TABLE I-continued

Structures of Some Mycolic Acids

| Mycolic acid | Strain |
|---|---|
| β-Mycolic acid | M. bovis BCG |

$$CH_3-(CH_2)_{17}-\underset{\underset{CH_3}{|}}{CH}-\underset{\underset{O}{\|}}{C}-(CH_2)_x-\underset{\diagdown\;\diagup}{CH-CH}-(CH_2)_y-\underset{\underset{C_{24}H_{49}}{|}}{CH}-\underset{\underset{}{|}}{\overset{\overset{OH}{|}}{CH}}-CO_2H$$

$$\underset{CH_2}{}$$

x = 11 to 21, y = 28 to 18   max. x + y = 39: $C_{90}H_{176}O_4$
                              min. x + y = 29: $C_{80}H_{156}O_4$

---

The synthesis of the 6,6'-diacyl esters of trehalose in accordance with presently preferred variants of the invention may be illustrated schematically by the following series of reactions:

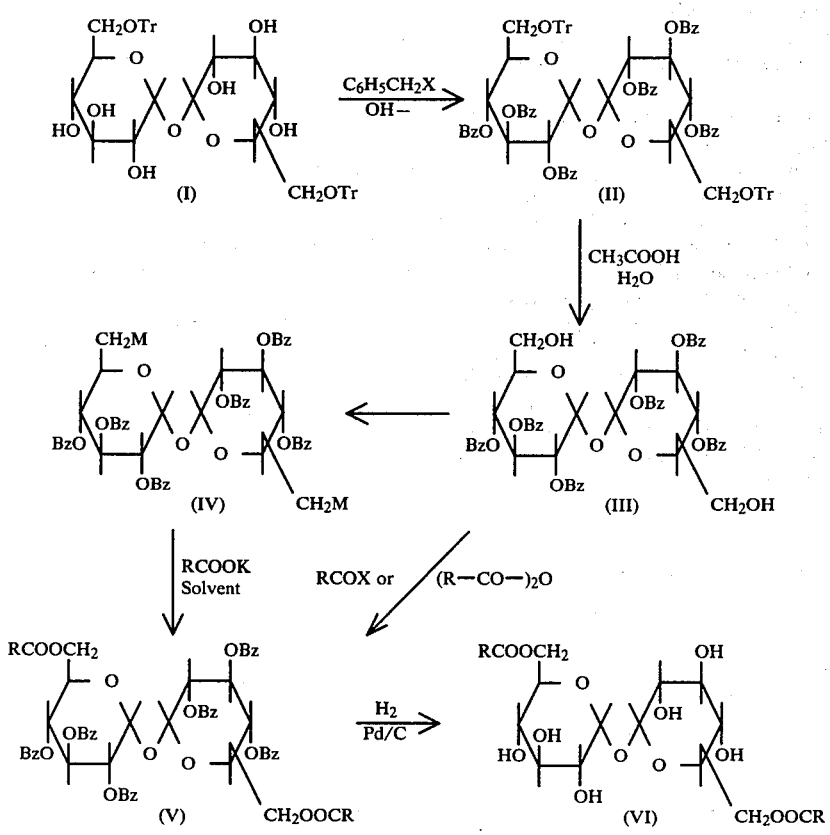

In the above formulae, X is halogen, Tr represents a monovalent trityl (triphenyl methyl) radical, Bz represents a monovalent benzyl radical, M represents a monovalent-O-mesyl, -O-tosyl, bromo or iodo radical, and R is a monovalent organic radical which, when taken with the carbon atom attached thereto, contains about 10–100 carbon atoms and preferably about 20–90 carbon atoms, and is the residue of a saturated or unsaturated and substituted or unsubstituted carboxylic acid.

The foregoing is a novel and highly improved synthesis of natural cord factors and other 6,6'-diacyl trehaloses which avoids the complications that plague the methods of the prior art. The synthesis scheme is far superior to the methods of the prior art in that acylations leading to isomers other than the 6,6'-diesters are dramatically reduced and anyhydro trehalose derivatives are not formed. Also, the esterification step to produce product V by reaction of product IV with a carboxylate salt may be forced by employing a substantial excess of the carboxylate salt due to product V being very easily and completely separated from the unreacted carboxylate salt, as compared with the difficult and rarely complete separations that characterize the prior art methods.

The presently preferred synthesis scheme involves the following series of steps.

Step 1. Anhydrous trehalose is converted into 6,6'-ditriphenyl methyl trehalose (6,6'-ditrityl trehalose) by reaction with a halotriphenyl methane, which is preferably chlorotriphenyl methane or bromotriphenyl methane, in the presence of a suitable solvent such as pyridine. This reaction is described by Bredereck in Berichte 63 B: 959–965 (1930), which is incorporated herein by reference. The resulting 6,6'-ditrityl trehalose (product I) is a known compound and is obtained in high yield. It may be easily rendered sufficiently pure for the succeeding step in the synthesis by conventional physical purification techniques of a routine nature.

Step 2. The 6,6'-ditrityl trehalose (product I) is converted into the novel compound 2,3,4,2',3',4'-hexa-O-benzyl-6,6'-ditrityl trehalose (product II) by treatment with an excess of a benzyl halide, which is preferably benzyl chloride or benzyl bromide, in the presence of a suitable solvent and a base, at an elevated reaction temperature, and for a sufficient period of time for the reaction to occur. The solvent is preferably dioxane or tetrahydrofuran, and the base is preferably an alkali metal hydroxide such as sodium hydroxide or potassium hydroxide. A suitable reaction temperature is between about 50° C. and the reflux temperature of the solvent, and the reaction time is usually about 0.5–6 hours. The reaction is preferably carried out under reflux for about one hour. The resulting product II is formed in high yield and may be recovered from the reaction mixture and easily rendered sufficiently pure for use in the subsequent step in the synthesis by conventional physical purification techniques of a routine nature. For example, crude product II may be recovered by evaporation of the reaction solvent and the reaction by-products and any unreacted material may be removed by steam distillation and/or vacuum distillation. Product II may be further purified when desired by chromatography on silica gel using, for example, equal volumes of ethyl ether and hexane as an eluent. As is well understood in this art, a wide variety of other prior art adsorbents and/or eluents of the proper polarity may be selected for the chromatographic purification. Examples of other absorbents include silicic acid and silicic acid-Celite ® mixtures, and examples of other eluents include hexane-chloroform and chloroform-methanol solvent mixtures.

Step 3. The 2,3,4,2',3',4'-hexa-O-benzyl-6,6'-ditrityl trehalose (product II) is converted into the novel compound 2,3,4,2',3',4'-hexa-O-benzyl trehalose (product III) by hydrolysis under mild conditions. Any suitable hydrolytic technique may be employed which is sufficiently mild to remove the trityl groups from the 6 and 6'-positions while retaining the benzyl groups in the 2,3,4,2',3',4'-positions. Hydrolysis in a weakly acidic aqueous solution at moderately elevated temperature and over a period of time sufficient to remove the trityl groups without disturbing the benzyl groups is usually preferred. Hydrolysis in 50–90% aqueous acetic acid and in the presence or absence of a strongly acidic catalyst, such as HCl or $BF_3$, usually gives very satisfactory results. The hydrolysis temperature and time may vary from about room temperature for two days to about 60°–90° C. for 3–12 hours in most instances. The best results are often achieved by hydrolysis in approximately 80% aqueous acetic acid at about 75°–80° C. for about 6–7 hours. Product III may be recovered by evaporating the reaction mixture to obtain a residue which is the crude product. The crude product may be purified easily by chromatography on silica gel. Traces of the reaction solvent, trityl salts and byproducts may be removed by elution with, for example, an eluent containing equal volumes of ethyl acetate and hexane. Continued elution with the same solvent mixture followed by elution with a solvent mixture containing, for example, two volumes of ethyl acetate to one volume of hexane results in the recovery of substantially pure 2,3,4,2',3',4'-hexa-O-benzyl trehalose (product III). Other prior art chromatographic purification techniques may be used if desired, such as those mentioned in Step 2.

Step 4-A. When desired, the 2,3,4,2',3', 4'-hexa-O-benzyl trehalose (product III) may be converted directly into the novel product V by acylation in the 6 and 6'-positions with a carboxylic acid halide, which is preferably the chloride, bromide or iodide, or with a carboxylic acid anhydride. As a general rule, well-established acylation procedures are satisfactory wherein a hydroxyl group is esterified by reaction with a carboxylic acid halide or anhydride.

Suitable solvents for acid chloride acylation include benzene and/or pyridine, and the solvemt may be present in a quantity sufficient to dissolve the reactants. The reaction temperature in a solvent may be about 25°–80° C. and usually is preferably about 60° C. The reaction time in a solvent may be about 1–5 hours, and often is preferably about 3 hours. Alternatively, the solvent may be omitted and the reaction may be carried out under a reduced pressure of about 1–10 mm Hg at a temperature sufficiently high to provide liquid state reactants, such as about 60°–80° C.

Suitable solvents for carboxylic acid anhydride acylation include pyridine and hydrocarbons such as benzene or toluene in the presence of an organic base such as pyridine or triethyl amine. The reaction temperature may be about 15°–60° C. and is preferably 30°–40° C., and the reaction time may be about 12–24 hours.

The desired 2,3,4,2',3', 4'-hexa-O-benzyl-6,6'-diacyl trehalose (product V) may be recovered from the reaction mixture and purified by chromatography on silica gel employing a solvent mixture containing, for example, two volumes of hexane to one volume of ethyl ether as the eulent. Other prior art chromatographic purification techniques may be used if desired, such as those mentioned in Step 2.

Step 4-B. Alternatively to step 4-A, the 2,3,4,2',3',4'-hexa-O-benzyl trehalose may be acylated in the 6 and 6'-positions by first converting it into the novel 6,6'-dimesyl, ditosyl, didesoxy dibromo or di-iodo derivative (product IV), which is then reacted with an excess of a carboxylic acid salt to produce the desired novel 2,3,4,2',3',4'-hexa-O-benzyl-6,6'-diacyl trehalose (product V). The 6,6'-dimesyl derivative may be prepared in nearly quantative yield by reacting mesyl chloride with product III in pyridine at room temperature for about 2 hours The 6,6'-ditosyl derivative may be prepared in high yield by reacting p-toluenesulfonyl chloride with product III in pyridine solution for about 18 hours. The 6,6'-dibromo and 6,6'-di-iodo derivatives may be prepared by reacting the above prepared 6,6'-dimesyl deriative with excess KBr or KI, respectively, in acetone solution at room temperature for 10–12 hours, or alternatively, by reacting product III directly with phosphorus tribromide or phosphorus iodide, respectively. Well established procedures may be employed in preparing the above derivatives.

Step 5. Product IV, which may be in the form of the 6,6'-dimesylate, ditosylate, dibromo or di-iodo derivative of 2,3,4,2',3',4'-hexa-O-benzyl trehalose, is converted into a wide variety of novel 6,6'-diesters of hexa-O-benzyl trehalose by heating with an excess of a salt of the desired carboxylic acid in a suitable solvent. Preferably, the sodium or potassium salt of the carboxylic acid is used in a 3–6 to 1 molar excess. Suitable solvents include toluene and hexamethyl phosphoric triamide. A satisfactory reaction temperature is about 65°–100° C. and is preferably 85°–95° C. The reaction time may be about 2–10 hours and is preferably 3–5 hours. Following acidification of the reaction mixture with, for example, hydrochloric acid and separation of the solvent, product V may be purified quite easily by chromatography on silica gel. Separation from the excess unreacted carboxylic acid is very simple due to the unreacted carboxylic acid being much more polar than the hexabenzylated-6,6'-diester of trehalose, which elutes in the first effluent from the chromatography column when employing, for example, a solvent mixture containing hexane and ethyl ether as the eluent. The excess carboxylic acid is recovered substantially quantitatively from the column by employing a much more polar eluent. Other prior art chromatographic purification techniques may be used if desired, such as those mentioned in Step 2.

Step 6. The purified hexa-O-benzyl trehalose 6,6'-diesters (product V) are hydrogenolyzed to produce the desired trehalose-6,6'-diacyl ester (product VI). Conventional hydrogenolysis techniques may be employed for this purpose. A hydrogen pressure of approximately 50 psi in the presence of a palladium-on-charcoal (carbon) catalyst at room temperature is satisfactory. If desired, higher hydrogen pressures and temperatures may be employed, with or without other process changes. The trehalose-6,6'-diacyl esters may be recovered as substantially pure homogeneous produces by chromatography on silica gel. The overall yield for the complete synthesis is about 25–30%, or an average of about 80% for each step, and this may be improved by recovery of products from incompletely purified fractions in Steps 5 and 6.

As a general rule, the solvents, reaction temperatures, reaction times, and other reaction variables used in the various steps of the foregoing synthesis may be in accordance with well established procedures for the general type of reaction that is involved in a given instance. For example, when desired the benzylation technique used to produce product II, the hydrolysis technique used to produce product III, the direct acylation technique used to produce product V from product III, the various techniques employed to produce the 6,6'-dimesyl, ditosyl, dibromo and di-iodo derivatives of product IV from product III and the use thereof to produce product V, and the hydrogenolysis of product V to produce product VI, may be in accordance with well established procedures and techniques for the general class of reaction that is involved in each step. Also, it is understood that the carboxylic acids used in preparing the carboxylic acid halides, anhydrides and salts for reaction with product III or IV to produce product V, are selected in accordance with the general discussion appearing hereinbefore to thereby satisfy the definition of R in the various structural formulae.

A number of the many advantages of the present invention may be summarized briefly as follows.

(1) The initial tritylation of trehalose occurs almost exclusively at the 6,6'-positions, and these positions are protected for later manipulation. The resulting 6,6'-di-O-trityl trehalose is obtained in high yield and requires only minimal purification.

(2) The benzylation of 6,6'-di-O-trityl trehalose to the fully hexabenzylated product is a surprisingly simple conversion. This could not be anticipated in view of the bulk of the triphenylmethyl groups at the 6,6'-positions which, from steric considerations, would be expected to interfere with a complete benzylation. The 2,3,4,2',3',4'-positions require blocking to prevent formation of anhydrotrehaloses in later steps in the process, and blocking with the highly non-polar benzyl groups facilitates subsequent chromatographic separations. Moreover, the benzyl groups are easily removed, when required, by a simple non-destructive hydrogenolysis.

(3) The detritylation to unblock the 6,6'-positions in the succeeding step following benzylation is simple and substantially non-destructive.

(4) The 2,3,4,2',3',4'-hexanbenzyl trehalose is easily purified and, in a variant of the present invention which is given in the experimental details, can be directly acylated with carboxylic acid chlorides, bromides, iodides or anhdyrides to give hexa-O-benzyl derivatives of 6,6'-diacyl trehaloses.

(5) The free 6,6'- hydroxyl groups can be quantitatively mesylated with methane sulfonly chloride, or p-toluene sulfonyl chloride can be used to introduce the tosyl radical as an alternative reactive group for subsequent displacement by acyl functions. However, in the preferred embodiment of the invention, the smaller and more reactive mesyl group is used. When desired, the 6,6'-hydroxyl groups may be replaced by bromo or iodo groups for subsequent displacement by acyl groups in excellent yield.

(6) The hexa-O-benzyl-6,6'-dimesylate of trehalose, a key intermediate in the synthesis scheme, has the very desirable property of high reactivity and ease of displacement at the 6,6'-positions. The non-polar and stable blocking groups at the remaining positions enhance solubility in mild non-polar solvents, prevent anhydrotrehalose formation, facilitate chromatographic separations, and are removed with ease by a simple hydrogenolysis that leaves the crucial ester functions at the 6,6'-positions undistubed. Also, its properties are such that replacement of the mesyl groups by lipid carboxylate anions is facilitated. A large excess of the latter can be used to drive the reaction as the desired diester product is easily purified and separated from the excess lipic carboxylic acids.

(7) The hydrogenolysis to produce the unblocked trehalose-6,6'-diesters proceeds under mild conditions and produces toluene as the second product of the reaction. Any incompletely hydrogenolyzed benzyl groups render the by-products easily separable from the polar hexahydroxy trehalose diester.

(8) The yields are very good and, due to the ease of the chromatographic separations, additional intermediate and final products can be recovered by rechromatography of incompletely purified fractions.

The 6,6'-diacyl esters of trehalose disclosed herein exhibit a number of biological activities and thus they are useful for these purposes. Examples of these biological activities are discussed in greater detail hereinafter.

Toxicity

Natural and synthetic cord factors, and even the much simpler synthetic analogs such as the dipalmitate and distearate, exert an unusual and characteristic toxicity in mice. A few repeated intraperitoneal injections of small amounts of the material dissolved in paraffin oil kills a majority of the animals, and especially C57 B1 and Dba mice. The present inventors have confirmed earlier observations in that young (12 to 14 g) C17 B1 mice, injected at 2 to 3 day intervals with 10 $\mu$g doses of highly purified cord factor of *M. tuberculosis,* undergo precipitous weight loss, and the mice begin to die after about a week. Lower molecular weight analogs such as trehalose-6,6'-dipalmitate or distearate are similarly active, but higher doses are required such as about 50 $\mu$g per injection.

Aside from an intense peritonitis, the most striking feature to be seen at necropsy of mice dying from cord factor intoxication is acute pulmonary hemorrhage. The mechanism of this activity is as yet only poorly understood. However cord factor does not appear to be toxic for rats, guinea pigs and higher animal forms.

Biochemical lesions are induced in cord factor intoxication and in tuberculosis, which were ultimately traced to a direct physical attack by the agents on mitochondrial membranes and mitochondria, especially of lung, liver and spleen. This may be demonstrated both in vivo and in vitro, with isolated mitochondrial preparations, and the attack results in a pathological, irreversible mitochondrial swelling with fragmentation of cristae. The biochemical consequences of the mitochondrial attack translate into a severe disturbance in electron flow along the mitochondrial respiratory chain and disruption of oxidative phosphorylation. This activity and its toxic manifestation are surprisingly sensitive to structural changes in the glycolipid molecule. They are destroyed by acetylation or permethylation. In synthetic analogs, substitution of sucrose or glucose for trehalose results in a marked attenuation but not in total abrogation of the activity. Substitution at the 6 position of the carbohydrate is stringently required as 1- and 2-mycoloyl glucose are devoid of toxicity. The stereochemical disposition of the hydroxyl groups at positions 2, 3, and 4 of 6-mycoloyl methyl glycosides critically affects the biological activity. Thus, it is very important that the synthetic products of the present invention be under rigid stereochemical control.

Adjuvant Activity

When dilute natural or synthetic cord factor solutions in mineral oil are emulsified in Tween ®-saline solution and injected intravenously into mice, the oil solution of glycolipid stimulates the formation of pulmonary granulomas. In mice the cord factor granuloma confers some protection against an intravenous challenge with virulent tubercle bacilli.

Oil solutions of cord factor emulsified in Tween-saline solution are adjuvant active in mice. Cord factor as a substitute for killed mycobacteria in Freund's complete adjuvant was more active than an equal weight of killed tubercle bacilli. It elicited delayed hypersensitivity to protein antigens in rats, but it was inactive when presented in this fashion to guinea pigs as is disclosed in *Infection and Immunity* 13:776-781 (1976). However, when presented in another fashion, cord factor also induces delayed hypersensitivity to protein antigens in this animal species, as is disclosed in *Journal of Immunology* 116:482-488 (1976).

Antitumor Activity

Based upon mechanisms that are not entirely understood, natural and synthetic trehalose-6,6'-dimycolates have emerged as a principal factor or cofactor in contributing to antitumor activity of a variety of preparations. This has been recognized and studied in a number of animal models as is disclosed on pages 63–193 of the text *Tuberculosis*; published by W. B. Saunders Co., Philadelphia (1979). Vaccines containing cell walls of mycobacteria, cord factor and mineral oil prepared as emulsions according to prior art methods disclosed in this text are currently being tested experimentally in humans in tumor immunotherapy, and experiments in humans with certain endotoxins and cord factor are planned. Both types of vaccines have been successfully exploited in the treatment of basal cell carcinoma in cattle, i.e., "Cancer Eye". In addition, an unguent comprised of heat-killed *M. bovis,* BCG, cord factor and vaseline is being successfully used in the treatment of several kinds of skin malignancies in humans, as is disclosed in *Dermatologia* 158:104-116; 117-125 (1979).

As is well understood in the art, the various structural formulae given herein for the trehalose core are abbreviated in a conventional manner for purposes of clarity and simplification. Thus, it is understood that each of the two rings of the trehalose molecule includes five carbon atoms positioned at the five indicated points and that each of the ring carbon atoms has a hydrogen atom attached thereto which is not shown.

The foregoing detailed description and the following specific examples are for purposes of illustration only, and are not intended to be limiting to the spirit or scope of the appended claims.

EXAMPLE I

This example illustrates the preparation of 6,6'-di-O-trityl trehalose by the process disclosed by Bredereck in Berichte, volume 63B (1930), pages 959–965, the disclosure of which is incorporated herein by reference.

In accordance with the above process, 3.9 grams of trehalose dihydrate was dehydrated by dissolving in 70 ml of pyridine and concentrating the solution of 30 ml in a rotary evaporator. This procedure removed the water of hydration by azeotropic distillation. The resulting concentrated solution was cooled to room temperature, and 7.38 grams of trityl chloride was added and the admixture was reacted at room temperature for 45 hours.

At the end of the reaction period, a 50—50 admixture of ice and water was added to precipitate the crude gummy reaction product. The crude product was admixed with 20-30 cc of ethyl alcohol, filtered, washed several times with water, and thereafter dried in air.

The dried crude gummy product was extracted with benzene, triturated with 90-100 cc of ethyl alcohol until it became crystalline, filtered and dried. The yield was 7.9 grams of 6,6'-di-O-trityl trehalose, which was 92% of the theoretical yield. The purified crystalline product was homogeneous as determined by thin layer chromatography and thus was of high purity, and was used as a reactant in Example II.

EXAMPLE II

This example illustrates the preparation of the novel compound 2,3,4,2',3',4'-hexa-O-benzyl-6,6'-di-O-trityl trehalose.

Freshly distilled benzyl chloride was added in an amount of 12 ml to a boiling mixture containing 1.26 grams of the 6,6'-di-O-trityl trehalose prepared in accordance with Example I, 10 grams of powdered potassium hydroxide and 12 ml of dioxane. The resulting reaction mixture was boiled gently under reflux for one hour, and then the dioxane was distilled off and the residue was allowed to cool to room temperature. A white massive precipitate formed in the cooled reaction product, and water was added in an amount to dissolve the precipitate. The reaction product was extracted twice with ether, and the ethereal solution was washed with water and dried over anhydrous sodium sulfate. The ether was evaporated from the dried ethereal solution, and the benzyl alcohol and dibenzyl ether by-products contained therein were removed by steam distillation and high vacuum distillation.

The resulting oily residual material was substantially pure 2,3,4,2',3', 4'-hexa-O-benzyl-6,6'-di-O-trityl trehalose. A small portion of this product was further purified by chromatography on silica gel using equal volumes of ether and hexane as the eluent. The analytically pure sample thus obtained had an optical rotation at a concentration of 0.7% in chloroform of $[\alpha]_D^{24} = +65°$.

EXAMPLE III

This example illustrates the preparation of the novel compound 2,3,4,2',3',4'-hexa-O-benzyl trehalose.

The crude oily 2,3,4,2',3',4'-hexa-O-benzyl-6,6'-di-O-trityl trehalose prepared in accordance with Example II was treated with 40 ml of 80% aqueous acetic acid at 75°–80° C. for 6.5 hours. Evaporation of the reaction mixture in a rotary evaporator gave an oily residue which was purified by chromatography using a column containing 70 grams of silica gel. Traces of the reaction solvent, trityl salts and minor by-products were removed by elution with an admixture containing equal volumes of ethyl acetate and hexane. Continued elution with this same solvent mixture followed by elution with a solvent mixture containing two volumes of ethyl acetate to one volume of hexane resulted in 0.93 gram of the desired 2,3,4,2',3',4'-hexa-O-benzyl trehalose in the form of a syrup. The yield was 69% based upon the amount of 6,6'-trityl trehalose used as a reactant in Example II. The optical rotation at a concentration of 1.0% in chloroform was $[\alpha]_D^{24°} = +99°$.

EXAMPLE IV

This example illustrates the preparation of 2,3,4,2',3',4'-hexa-O-benzyl-6,6'-di-O-mesyl trehalose, which is a novel compound.

Methane sulfonyl chloride was added in an amount of 0.75 ml to a cold (ice bath) solution containing 0.52 g of 2,3,4,2',3',4'-hexa-O-benzyl trehalose prepared in accordance with Example III in 8 ml of pyridine. The resulting reaction mixture was stirred for 2 hours at room temperature, and then ice water was added and the mixture was extracted with ethyl acetate. The ethyl acetate solution was washed successively with 2 M HCl (3 times), water, saturated sodium bicarbonate solution, and finally water. The washed ethyl acetate solution was dried over anhydrous sodium sulfate, and the entire solution was evaporated to produce the desired 2,3,4,2',3',4'-hexa-O-benzyl-6,6'-di-O-mesyl trehalose as a syrup. The yield was 0.6 gram, i.e., 98% of the theoretical yield. The product was found to be homogeneous by thin layer chromatography using a developing solvent mixture containing three volumes of ethyl acetate to one volume of hexane. The optical rotation at a concentration of 1.47% in chloroform was $[\alpha]_D^{24} = +86°$. The nuclear magnetic resonance spectrum (NMR) of this product was in accordance with the assigned structure for 2,3,4,2',3',4'-hexa-O-benzyl-6,6'-di-O-mesyl trehalose.

EXAMPLE V

This example illustrates the preparation of the novel compound 2,3,4,2',3',4'-hexa-O-benzyl-6,6'-di-O-[p-(hexadecyloxy-phenyl)-4-butyryl]-trehalose.

A reaction mixture containing 80 mg of the 2,3,4,2',3',4'-hexa-O-benzyl-6,6'-di-O-mesyl trehalose prepared in accordance with Example IV and 0.18 g of the potassium salt of para-hexadecyloxy-phenyl-4-butyric acid in 3 ml of hexamethyl phosphoric triamide was stirred for three hours at a temperature of 95°–100° C. Ice was then added, and the cooled reaction mixture was acidified with 2 M HCl. The resulting precipitate consisting of the unreacted acid and the desired reaction product was isolated by centrifugation. The precipitate was washed several times with water and then dried.

The solid residue was applied to a column containing 40 grams of silica gel, and the desired product was eluted with a solvent mixture containing two volumes of hexane to one volume of ethyl ether. The desired 2,3,4,2',3',4'-hexa-O-benzyl-6,6'-di-O-[p-(hexadecyloxy-phenyl)-4-butyryl]-trehalose was isolated as a homogeneous syrup in a yield of 109 mg, which was 85% of the theoretical yield. The optical rotation at a concentration of 1.90% in chloroform was $[\alpha]_D^{24} = +54°$. The nuclear magnetic resonance spectrum (NMR) was in accordance with the assigned structure.

EXAMPLE VI

This example illustrates the preparation of the novel compound 2,3,4,2',3',4'-hexa-O-benzyl-6,6'-di-O-corynomycolyl trehalose.

Potassium corynomycolate was prepared according to the procedure published in *Bulletin Societe Chimie de France*, (1954), pages 504–510. An excess thereof was used to treat 2,3,4,2', 3',4'-hexa-O-benzyl-6,6'-di-O-mesyl-trehalose, which was previously prepared in accordance with Example IV. Hexamethylphosphoric triamide was used as a solvent, and the procedure described in Example V was followed to thereby produce the corresponding 6,6'-diester derivative.

The resulting reaction product was purified by chromatography on silica gel using a solvent mixture containing 3 volumes of hexane to 2 volumes of ethyl ether as the eluent. The purified product was isolated as a homogeneous syrup in a yield of 82%, and it was entirely free of corynomycolic acid. Unreacted corynomycolic acid was recovered in good yield when the silica gel column was eluted with a solvent mixture containing 9 volumes of chloroform to one volume of methyl alcohol. The desired homogeneous 2,3,4,2',3',4'-hexa-O-benzyl-6,6'-di-O-corynomycolyl trehalose thus obtained had an optical rotation of $[\alpha]_D^{25} = +45.3°$ at a concentration of 0.64% in chloroform.

EXAMPLE VII

This example illustrates the preparation of novel 2,3,4,2',3',4'-hexa-O-benzyl-6,6'-di-O-mycolyl trehalose.

The 2,3,4,2',3',4'-hexa-O-benzyl-6,6'-di-O-mesyl trehalose prepared in accordance with Example IV was treated with a large excess of potassium mycolate following the general procedures described in Examples V and VI. The potassium mycolate was obtained from the alkaline hydrolysis and extraction of *Mycobacterium bovis* following the general known procedures described by A. H. Etemadi, Thesis: University of Paris, 1965.

The reaction product was recovered as described in Examples V and VI. It was isolated as a homogeneous syrup in 72% yield after chromatography on silica gel using a solvent mixture containing two volumes of hexane to one volume of ether as an eluent. The product was free of contaminating mycolic acid, which was subsequently recovered by elution of the chromatography column with a solvent mixture containing two volumes of ethyl ether to one volume of hexane. The 2,3,4,2',3',4'-hexa-O-benzyl-6,6'-di-O-mycolyl trehalose thus obtained had an optical rotation of $[\alpha]_D^{28} = +32°$ at a concentration of 1.1% in chloroform.

EXAMPLE VIII

This example illustrates the preparation of 6,6'-di-O-[p-(hexadecyloxy-phenyl)-4-butyryl]-trehalose which is a novel compound.

A solution of 135 mg of 2,3,4,2',3',4'-hexa-O-benzyl-6,6'-di-O-[p-(hexadecyloxy-phenyl)-4-butyryl]-trehalose in 50 ml of a solvent mixture containing one volume of ethyl acetate to one volume of ethyl alcohol was hydrogenated at a pressure of 50 psi and at room temperature for five hours in the presence of 110 mg of a 10% Pd/C catalyst. The catalyst was filtered off and washed several times with chloroform. The filtrate was evaporated to give 66 mg of a white solid crude reaction product, which was 72% of the theoretical yield.

The crude product was crystallized from ethyl alcohol to give 51 mg of purified product having a melting point of 158°–160° C., which was 56% of the theoretical yield. The product in the mother liquor may be recycled for rechromatography and recovery. The desired 6,6'-di-O-[p-(hexadecyloxy-phenyl)-4-butyryl]-trehalose had an optical rotation of $[\alpha]_D^{24} = +53°$ at a concentration of 0.73% in chloroform.

EXAMPLE IX

This example illustrates the preparation of the novel compound 6,6'-di-O-[3,4-di-(hexadecyloxy-phenyl)-γ-butyryl]-trehalose.

The general procedures of Examples V and VIII are followed with the exception of substituting the potassium salt of 3,4-di-hexadecyloxy-phenyl-γ-butyric acid for the potassium salt of p-hexadecyloxy-phenyl-4-butyric acid. The resulting product is the desired 6,6'-di-O-[3,4-di-(hexadecyloxy-phenyl)-γ-butyryl]-trehalose.

The product of this example exhibited antitumor activity in the mouse fibrosarcoma model, as described in the *International Journal of Cancer*, Volume 19, pages 818-821 (1977), equal to that of natural cord factor prepared from *M. tuberculosis*.

EXAMPLE X

This example illustrates the preparation of 6,6'-di-O-corynomycolyl trehalose.

The 2,3,4,2',3',4'-hexa-O-benzyl-6,6'-di-O-corynomycolyl trehalose prepared in accordance with Example VI was hydrogenated in accordance with the procedure described in Example VIII. The resulting crude cord factor product was purified by chromatography on silica gel using a solvent mixture containing 9 volumes of chloroform to one volume of methanol as an eluent.

The yield of the desired purified product 6,6'-di-O-corynomycolyl trehalose was 52 mg in the form of a homogeneous waxy material having an optical rotation of $[\alpha]_D^{24} = +50.4°$ at a concentration of 0.87% in chloroform. The infrared spectrum thereof was identical with that of an authentic sample. Its nuclear magnetic resonance spectrum (NMR) was in accordance with the assigned structure. Its biological activity in the mouse fibrosarcoma model described in the *International Journal of Cancer*, Volume 19, pages 818-821 (1977), was excellent.

EXAMPLE XI

This example illustrates the preparation of 6,6'-di-O-mycolyl trehalose, which is the cord factor of *M. bovis*.

Hydrogenolysis of 2,3,4,2',3',4'-hexa-O-benzyl-6,6'-di-O-mycolyl trehalose prepared in accordance with Example VII was carried out as described in Examples VIII and X. The crude product was applied to a silica gel column using a solvent mixture containing 9 volumes of chloroform and one volume of methanol as an eluent.

The desired purified 6,6'-di-O-mycolyl trehalose was obtained as a waxy solid which had an optical rotation of $[\alpha]_D^{28}=+37°$ at a concentration of 0.8% in chloroform. In thin layer chromatography, its mobility was identical with a natural cord factor obtained from *Mycobacterium tuberculosis,* strain "Peurois", and it was free of contaminant mycolic acid. Also, its infrared spectrum was identical with that of highly purified natural cord factor (see *Recent Results in Cancer Research,* Volume 47, pages 251-258 (1974)).

EXAMPLE XII

This example illustrates the preparation of the novel compound 2,3,4,2',3',4'-hexa-O-benzyl-6,6'-di-tosyl trehalose.

To a solution of 207 mg of 2,3,4,2',3',4'-hexa-O-benzyl trehalose in 3 ml of pyridine was added 220 mg of p-toluenesulfonyl chloride, and the resulting reaction mixture was stirred for 18 hours at a temperature of 24° C. Ice and water was added, and the reaction mixture was extracted with ethyl acetate. The ethyl acetate solution was separated and washed successively with 2 M HCl (3 times), water, saturated sodium bicarbonate solution, and finally water. The washed ethyl acetate solution was dried over anhydrous sodium sulfate, and the dried solution was evaporated to obtain 203 mg of the desired 2,3,4,2',3',4'-hexa-O-benzyl-6,6'-di-O-tosyl trehalose as a syrup. The product was found to be homogeneous by thin layer chromatography using a developing solvent mixture containing three volumes of ethyl acetate to one volume of hexane. The optical rotation was $[\alpha]_D^{24}=+73.2°$ at a concentration of 1.34% in chloroform.

Upon substituting the above prepared 2,3,4,2',3',4'-hexa-O-benzyl-6,6'-di-O-tosyl trehalose for the 2,3,4,2',3',4'-hexa-O-benzyl-6,6'-di-O-mesyl trehalose used in Examples V, VI, VII and IX, comparable results are obtained. While the mesyl and tosyl derivatives may be used interchangeably, usually the mesyl derivative is preferred.

EXAMPLE XIII

This example illustrates an alternative process employing acid chloride acylation for the preparation of the novel compound 2,3,4,2',3',4'-hexa-O-benzyl-6,6'-di-O-[p-(hexadecyloxy-phenyl)-4-butyryl]-trehalose.

To a suspension of 0.4 g of p-hexadecyloxyphenyl-4-butyric acid in 5 ml of benzene was added 0.2 ml of dimethylformamide, 0.15 ml of triethyl amine, and 0.4 ml of thionyl chloride. The resulting mixture was reacted in a stoppered flask at room temperature for 16 hours. At the end of the reaction period, the volatiles were evaporated under nitrogen and the residue was extracted into benzene. The extract was filtered and the benzene was evaporated to yield 0.4 g of the acid chloride derivative of p-hexadecyloxy-phenyl-4-butyric acid.

Without further purification, 0.3 g of the acid chloride derivative of p-hexadecyloxy-phenyl-4-butyric acid was reacted for 3 hours at a temperature of 60° C. with 0.17 g of 2,3,4,2',3',4'-hexa-O-benzyl trehalose dissolved in 5 ml of benzene in the presence of 2 mg of p-toluene sulfonic acid. The reaction mixture was then cooled to room temperature, diluted with ethyl acetate, washed with saturated aqueous sodium bicarbonate solution, and then washed with water. The washed reaction mixture was dried over anhydrous sodium sulfate, and the benzene, ethyl acetate and other volatiles were evaporated. The resulting product was purified by chromatography on a silica gel column, and the yield of 2,3,4,2',3',4'-hexa-O-benzyl-6,6'-di-O-[p-(hexadecyloxy-phenyl)-4-butyryl]-trehalose was 178 mg. The physical and chemical properties of the product and the NMR spectrum are in accordance with the product of Example V.

Alternatively, the acylation step of this example may be conducted in pyridine solution at 25°-40° C. for about 24 hours in the absence of the p-toluene sulfonic acid.

EXAMPLE XVI

This example illustrates the preparation of 2,3,4,2',3',4'-hexa-O-benzyl-6,6'-di-bromo-6.6'-didesoxy trehalose and 2,3,4,2',3',4'-hexa-O-benzyl-6,6'-di-iodo-6,6'-didesoxy trehalose, which are novel compounds. In one run, one mole of 2,3,4,2',3',4', -hexa-O-benzyl-6,6'-di-O-mesyl trehalose is reacted following well established procedures with excess potassium bromide (2.5–3.0 moles) in acetone solution at room temperature for 10–12 hours to obtain the desired 2,3,4,2',3',4',-hexa-O-benzyl-6,6'-dibromo-6,6'-didesoxy trehalose. In another run, potassium iodide is substituted for the potassium bromide in the above run, to thereby obtain the desired 2,3,4,2',3',4'-hexa-O-benzyl-6,6'-di-iodo-6,6'-didesoxy trehalose.

Upon substituting the above prepared 2,3,4,2',3'4'-hexa-O-benzyl-6,6'-dibromo-6,6'-didesoxy trehalose or 2,3,4,2',3',4'-hexa-O-benzyl-6,6'-di-iodo-6,6'-didesoxy trehalose for the 2,3,4,2',3',4'-hexa-O-benzyl-6,6'-di-O-mesyl trehalose used in Examples V, VI, VII and IX, comparable results are obtained. While the dibromo, di-iodo and mesyl derivatives may be used interchangeably, usually the mesyl derivative is preferred.

EXAMPLE XVII

This example illustrates an alternative process employing carboxylic acid anhydride acylation for the preparation of 2,3,4,2',3',4'-hexa-O-benzyl-6,6'-diacyl trehaloses, and the hydrogenation thereof to produce 6,6'-diacyl trehaloses.

One mole of stearic anhydride is reacted with 0.45 mole of 2,3,4,2',3',4'-hexa-O-benzyl trehalose in pyridine solution at a temperature of 50°-60° C. for 24 hours. Thereafter the desired 2,3,4,2',3',4', -hexa-O-benzyl-di-O-stearyl trehalose is recovered from the reaction mixture following well established procedures and hydrogenated following the general procedure of Example XI to produce 6,6'-di-O-stearyl trehalose.

In a second run, the above procedure is repeated with the exception of substituting palmitic anhydride for the stearic anhydride to thereby obtain 2,3,4,2',3',4',-hexa-O-benzyl-di-O-palmityl trehalose, which is then hydrogenated to produce 6,6'-di-O-palmityl trehalose.

We claim:

1. A compound selected from the group consisting of
 I. Compounds having the following structural formula

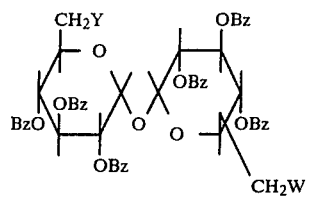

wherein Y and W are monovalent radicals selected from the group consisting of -O-trityl, -O-H, -O-mesyl, -O-tosyl, desoxy bromo, desoxy iodo, and -O-acyl radicals containing 10–100 carbon atoms, and Bz in each instance is a monovalent benzyl radical;
 II. 6,6'-di-O-[p-(hexadecyloxy-phenyl)-4-butyryl]-trehalose; and
 III. 6,6'-di-O-[3,4-di-(hexadecyloxy-phenyl)-γ-butyryl]-trehalose.

2. A compound in accordance with claim 1 wherein the said compound is 2,3,4,2',3',4'-hexa-O-benzyl-6,6'-di-O-trityl trehalose.

3. A compound in accordance with claim 1 wherein the said compound is 2,3,4,2',3',4'-hexa-O-benzyl trehalose.

4. A compound in accordance with claim 1 wherein the said compound is 2,3,4,2',3',4'-hexa-O-benzyl-6,6'-di-O-mesyl trehalose.

5. A compound in accordance with claim 1 wherein the said compound is 2,3,4,2',3',4'-hexa-O-benzyl-6,6'-di-O-tosyl trehalose.

6. A compound in accordance with claim 1 wherein the said compound is 2,3,4,2',3',4'-hexa-O-benzyl-6,6'-didesoxy-dibromo trehalose.

7. A compound in accordance with claim 1 wherein the said compound is 2,3,4,2',3',4'-hexa-O-benzyl-6,6'-didesoxy-di-iodo trehalose.

8. A compound in accordance with claim 1 wherein the said compound is 2,3,4,2',3',4'-hexa-O-benzyl-6,6'-di-O-[p-(hexadecyloxy-phenyl)-4-butyryl]-trehalose.

9. A compound in accordance with claim 1 wherein the said compound is 2,3,4,2',3',4'-hexa-O-benzyl-6,6'-di-O-corynomycolyl trehalose.

10. A compound in accordance with claim 1 wherein the said compound is 2,3,4,2',3',4'-hexa-O-benzyl-6,6'-di-O-mycolyl trehalose.

11. A compound in accordance with claim 1 wherein the said compound is 2,3,4,2',3',4'-hexa-O-benzyl-6,6'-di-O-[3,4-di-(hexadecyloxy-phenyl)-γ-butyryl]-trehalose.

12. A compound in accordance with claim 1 wherein the said compound is 6,6'-di-O-[p-(hexadecyloxy-phenyl)-4-butyryl]-trehalose.

13. A compound in accordance with claim 1 wherein the said compound is 6,6'-di-O-[3,4-di-(hexadecyloxy-phenyl)-γ-butyryl]-trehalose.

14. A compound in accordance with claim 1 wherein the said compound is 2,3,4,2',3',4'-hexa-O-benzyl-6,6'-di-O-acyl trehalose and the said acyl groups contain 10–100 carbon atoms.

15. A compound in accordance with claim 14 wherein the acyl groups are derived from mycolic acid.

16. A compound in accordance with claim 14 wherein the acyl groups are derived from corynomycolic acid.

17. A compound in accordance with claim 14 wherein the acyl groups are derived from p-hexadecyloxy-phenyl-4-butyric acid.

18. A compound in accordance with claim 14 wherein the acyl groups are derived from 3,4-di-(hexadecyloxy-phenyl)-γ-butyric acid.

19. A compound in accordance with claim 14 wherein the acyl groups are derived from a hydroxy carboxylic acid selected from the group consisting of threo-alpha-organobranched-beta-hydroxy carboxylic acid and erythro-alpha-organobranched-beta-hydroxy carboxylic acid.

20. A compound in accordance with claim 19 wherein the said alpha-organobranch of the carboxylic acid contains 10–28 carbon atoms and the remainder of the carboxylic acid molecule contains 12–30 carbon atoms.

21. A process for preparing 6,6'-diacyl esters of trehalose comprising dehexabenzylating 2,3,4,2',3',4'-hexa-O-benzyl-6,6'-di-O-acyl trehalose by hydrogenolysis with gaseous elemental hydrogen under pressure, the acyl groups containing 10–100 carbon atoms, the reactants in the said hydrogenolysis consisting essentially of the said 2,3,4,2',3',4'-hexa-O-benzyl-6,6'-di-O-acyl trehalose and elemental hydrogen, the said 2,3,4,2',3',4'-hexa-O-benzyl-6,6'-di-O-acyl trehalose being reacted with elemental hydrogen in the said hydrogenolysis to thereby remove all of the six benzyl radicals thereof and replace them with hydrogen and thereby produce a reaction mixture containing the corresponding 6,6'-diacyl ester of trehalose as the desired product and toluene as the by-product, and thereafter isolating the desired 6,6'-diacyl ester of trehalose thus produced from the reaction mixture.

22. The process of claim 21 wherein the said acyl groups are derived from carboxylic acids selected from the group consisting of mycolic acid, corynomycolic acid, p-hexadecyloxy-phenyl-4-butyric acid and 3,4-dihexadecyloxy-phenyl-γ-butyric acid.

23. The process of claim 21 wherein the said acyl groups are derived from mycolic acid.

24. The process of claim 21 wherein the said acyl groups are derived from corynomycolic acid.

25. The process of claim 22 wherein the acyl groups are derived from a hydroxy carboxylic acid selected from the group consisting of threo-alpha-organobranched-beta-hydroxy carboxylic acid and erythroalpha-organobranched-beta-hydroxy carboxylic acid.

26. The process of claim 25 wherein the said alpha-organobranch of the carboxylic acid contains 10–28 carbon atoms and the remainder of the carboxylic acid molecule contains 12–30 carbon atoms.

27. A process for preparing the compound 2,3,4,2',3',4'-hexa-O-benzyl-6,6'-di-O-acyl trehalose comprising acylating 2,3,4,2',3',4'-hexa-O-benzyl trehalose in each of the 6 and 6' positions with an acylating agent selected from the group consisting of carboxylic acid halides and carboxylic acid anhydrides containing 10–100 carbon atoms to thereby produce 2,3,4,2',3',4'-hexa-O-benzyl-6,6'-di-O-acyl trehalose containing impurities, and separating the 2,3,4,2',3',4'-hexa-O-benzyl-6,6'-di-O-acyl trehalose thus produced from the impurities by chromatography to produce purified 2,3,4,2'3',4'-hexa-O-benzyl-6,6'-di-O-acyl trehalose.

28. The process of claim 27 wherein the said 2,3,4,2',3',4'-hexa-O-benzyl trehalose is prepared by hydrolyzing 2,3,4,2',3',4'-hexa-O-benzyl-6,6'-di-O-trityl trehalose in an acidic aqueous medium to remove the trityl groups from the 6 and 6' positions without disturbing the benzyl groups in the 2,3,4,2',3',4'-positions to thereby produce 2,3,4,2',3',4'-hexa-O-benzyl trehalose containing impurities, and thereafter the 2,3,4,2',3',4'-hexa-O-benzyl trehalose thus produced is separated from impurities by chromatography.

29. The process of claim 28 wherein the said 2,3,4,2',3',4'-hexa-O-benzyl-6,6'-di-O-trityl trehalose is prepared by benzylating 6,6'-di-O-trityl trehalose in the 2,3,4,2',3',4'-positions by reacting with benzyl halide in organic solvent solution, the said 2,3,4,2',3',4'-hexa-O-benzyl trehalose being reacted in the presence of a stoichiometric excess of benzyl halide and a base to thereby produce 2,3,4,2',3',4'-hexa-O-benzyl-6,6'-di-O-trityl trehalose.

30. A process for preparing the compound 2,3,4,2',3',4'-hexa-O-benzyl-6,6'-di-O-acyl trehalose comprising acylating a compound selected from the group consisting of the 6,6'-di-O-mesyl, di-O-tosyl, didesoxy dibromo and di-iodo derivatives of 2,3,4,2',3',4'-hexa-O-benzyl trehalose in each of the 6 and 6'-positions by reacting with a salt of a carboxylic acid containing 10–100 carbon atoms, the said compound being reacted in organic solvent solution in the presence of a stoichiometric excess of the said carboxylic acid salt to thereby produce 2,3,4,2',3',4'-hexa-O-benzyl-6,6'-di-O-acyl trehalose containing impurities, and separating the 2,3,4,2',3',4'-hexa-O-benzyl-6,6'-di-O-acyl trehalose thus produced from the impurities by chromatography to produce purified 2,3,4,2',3',4'-hexa-O-benzyl-6,6'-di-O-acyl trehalose.

31. The process of claim 30 wherein the said 6,6'-di-O-mesyl, di-O-tosyl, didesoxy dibromo and di-iodo derivatives of 2,3,4,2',3',4'-hexa-O-benzyl trehalose are prepared by reacting 2,3,4,2',3',4'-hexa-O-benzyl trehalose in the 6 and 6' positions with mesyl halide, tosyl halide, phosphorus bromides and phosphorus iodide, respectively.

32. The process of claim 31 wherein the said 2,3,4,2',3',4'-hexa-O-benzyl trehalose is prepared by hydrolyzing 2,3,4,2',3',4'-hexa-O-benzyl-6,6'-di-O-trityl trehalose in an acidic aqueous medium to remove the trityl groups from the 6 and 6' positions without disturbing the benzyl groups in the 2,3,4,2',3',4'-positions to thereby produce 2,3,4,2',3',4'-hexa-O-benzyl trehalose containing impurities, and thereafter the 2,3,4,2',3',4'-hexa-O-benzyl trehalose thus produced is separated from impurities by chromatography.

33. The process of claim 32 wherein the said 2,3,4,2',3',4'-hexa-O-benzyl-6,6'-trityl trehalose is prepared by benzylating 6,6'-di-O-trityl trehalose in the 2,3,4,2',3',4'-positions by reacting with benzyl halide in organic solvent solution, the said 6,6'-di-O-trityl trehalose being reacted in the presence of a stoichiometric excess of benzyl halide and a base at elevated temperature and for a period of time to thereby produce 2,3,4,2',3',4'-hexa-O-benzyl-6,6'-di-O-trityl trehalose.

34. A process for preparing the compound 2,3,4,2',3',4'-hexa-O-benzyl trehalose comprising hydrolyzing 2,3,4,2',3',4'-hexa-O-benzyl-6,6'-di-O-trityl trehalose in an acid aqueous medium to remove the trityl groups from the 6 and 6' positions without disturbing the benzyl groups in the 2,3,4,2',3',4'-positions to thereby produce 2,3,4,2',3',4'-hexa-O-benzyl trehalose containing impurities, the aqueous medium being acidified with an acid which does not permanently enter into the hydrolysis reaction and the reactants in the said hydrolysis consisting essentially of the said 2,3,4,2',3',4'- hexa-O-benzyl-6,6'-di-O-trityl trehalose and the acidic aqueous medium, and separating the 2,3,4,2',3',4'-hexa-O-benzyl trehalose thus produced from impurities by chromatography.

35. The process of claim 34 wherein the said 2,3,4,2',3',4'-hexa-O-benzyl-6,6'-di-O-trityl trehalose is prepared by benzylating 6,6'-di-O-trityl trehalose in the 2,3,4,2',3',4'-positions by reacting with benzyl halide in organic solvent solution, the said 6,6'-di-O-trityl trehalose being reacted in the presence of a stoichiometric excess of benzyl halide and a base at elevated temperature and for a period of time to thereby produce 2,3,4,2',3',4'-hexa-O-benzyl-6,6'-di-O-trityl trehalose.

* * * * *